US009364549B2

(12) United States Patent
Voigt et al.

(10) Patent No.: US 9,364,549 B2
(45) Date of Patent: Jun. 14, 2016

(54) HYDROPHOBIC DRUG-DELIVERY MATERIAL, METHOD FOR MANUFACTURING THEREOF AND METHODS FOR DELIVERY OF A DRUG-DELIVERY COMPOSITION

(76) Inventors: Andreas Voigt, Berlin (DE); Jörg Kriwanek, Berlin (DE); Scott Hampton, Cumming, GA (US); Andreas Reiff, San Marino, CA (US); Sonja Ludwig, Berlin (DE)

( * ) Notice: Subject to any disclaimer, the term of this patent is extended or adjusted under 35 U.S.C. 154(b) by 0 days.

(21) Appl. No.: 13/307,506

(22) Filed: Nov. 30, 2011

(65) Prior Publication Data

US 2013/0136775 A1 May 30, 2013

(51) Int. Cl.
| | |
|---|---|
| A61K 39/00 | (2006.01) |
| A61K 47/44 | (2006.01) |
| A61K 47/10 | (2006.01) |
| A61K 47/12 | (2006.01) |
| A61K 47/14 | (2006.01) |
| C07K 16/00 | (2006.01) |
| A61K 47/46 | (2006.01) |
| A61K 9/06 | (2006.01) |
| A61K 9/14 | (2006.01) |
| A61K 47/02 | (2006.01) |
| A61K 47/22 | (2006.01) |

(52) U.S. Cl.
CPC . *A61K 47/46* (2013.01); *A61K 9/06* (2013.01); *A61K 9/14* (2013.01); *A61K 39/00* (2013.01); *A61K 47/02* (2013.01); *A61K 47/10* (2013.01); *A61K 47/12* (2013.01); *A61K 47/14* (2013.01); *A61K 47/22* (2013.01); *A61K 47/44* (2013.01); *C07K 16/00* (2013.01)

(58) Field of Classification Search
CPC ....... A61K 39/00; A61K 47/44; A61K 47/10; A61K 47/12; A61K 47/14; A61K 9/06; C07K 16/00
See application file for complete search history.

(56) References Cited

U.S. PATENT DOCUMENTS

| | | | | |
|---|---|---|---|---|
| 4,439,420 A | * | 3/1984 | Mattei et al. | 424/78.38 |
| 4,650,665 A | * | 3/1987 | Kronenthal et al. | 424/435 |
| 4,803,082 A | | 2/1989 | Cherukuri et al. | |
| 4,837,381 A | | 6/1989 | Steber et al. | |
| 5,700,410 A | * | 12/1997 | Nakamichi et al. | 264/122 |
| 6,355,272 B1 | | 3/2002 | Caramella et al. | |
| 2002/0160982 A1 | | 10/2002 | Jacobs et al. | |
| 2003/0091651 A1 | * | 5/2003 | Xu | 424/539 |

FOREIGN PATENT DOCUMENTS

EP 0 448 930 A1 10/1991

OTHER PUBLICATIONS

Watano et al. "Development of a Novel Vertical High Shear Kneader and Its Performance in Wet Kneading of Pharmaceutical Powders" Chem. Pharm. Bull. (2002) vol. 50, No. 3, pp. 341-345.*
Wang et al. "Protein aggregation-Pathways and influencing factors" International Journal of Pharmaceutics (2010), vol. 390, pp. 89-99.*
Abe, Hidaka, et al., "Rheological Analysis and Quantitative Evaluation of Wet Kneaded Wax Matrix", Chem. Pharm. Bull, 52(5): 510-516 (2004).
Aburahma, Mona H., et al., Preparation and In Vitro/In Vivo Characterization of Porous Sublingual Tablets Containing Ternary Kneaded Solid System of Vinpocetine with β-Cyclodextrin and Hydroxy Acid:, Sci. Pharm., 78: 363-379 (2010).
De Azevedo, Mariangela de Burgos M, et al., "New formulation of an old drug in hypertension treatment: the sustained release of caoptopril from cyclodextrin nanoparticles", International Journal of Nanomedicine, 6: 1005-1016 (2011).
Patel, Rakesh, et al., "Formulation Development and Process Optimization of Theophylline Sustained Release Matrix Tablet", International Journal of Pharmacy and Pharmaceutical Sciences, 1(2): 30-42 (2009).
Vlierberghe, S. Van, et al., "Biopolymer-Based Hydrogels as Scaffolds for Tissue Engineering Applications: A Review", Biomacromolecules, 12: 1387-1408 (2011).
Watano, Satoru, et al., "Development of a Novel Vertical High Shear Kneader and Its Perfomance in Wet Kneading of Pharmaceutical Powders", Chem. Pharm. Bull., 50(3) 341-345 (2002).

* cited by examiner

*Primary Examiner* — Abigail Fisher
*Assistant Examiner* — Daniel Branson
(74) *Attorney, Agent, or Firm* — Bibby, McWilliams & Kearney, PLLC; John K. Weatherspoon; Shilpa G. Ghurye

(57) ABSTRACT

A method for manufacturing a drug-delivery composition includes providing at least a pharmaceutically active composition, providing a hydrophobic matrix; and mixing the hydrophobic matrix and the pharmaceutically active composition to form a paste-like or semi-solid drug-delivery composition.

18 Claims, 3 Drawing Sheets

HYDROPHOBIC DRUG-DELIVERY MATERIAL, METHOD FOR MANUFACTURING THEREOF AND METHODS FOR DELIVERY OF A DRUG-DELIVERY COMPOSITION

FIELD OF THE INVENTION

The present invention belongs to the field of controlled drug release, particularly to methods for manufacturing drug-delivery compositions including pharmaceutically active substances or compounds, and to the controlled delivery thereof into living organisms and tissues for therapeutic purposes.

BACKGROUND OF THE INVENTION

Most therapeutic dosage forms include mixtures of one or more active pharmaceutical ingredients (APIs) with additional components referred to as excipients. APIs are substances that exert a pharmacological effect on a living tissue or organism, whether used for prevention, treatment, or cure of a disease. APIs can be naturally occurring or synthetic substances, or can be produced by recombinant methods, or any combination of these approaches.

Numerous methods have been devised for delivering APIs into living organisms, each with more or less success. Traditional oral therapeutic dosage forms include both solids (tablets, capsules, pills, etc.) and liquids (solutions, suspensions, emulsions, etc.). Parenteral dosage forms include solids and liquids as well as aerosols (administered by inhalers, etc.), injectables (administered with syringes, micro-needle arrays, etc.), topicals (foams, ointments, etc.), and suppositories, among other dosage forms. Although these dosage forms might be effective in delivering low molecular weight APIs, each of these various methods suffers from one or more drawbacks, including the lack of bioavailability as well as the inability to completely control either the spatial or the temporal component of the API's distribution when it comes to high molecular weight APIs. These drawbacks are especially challenging for administering biotherapeutics, i.e. pharmaceutically active peptides (e.g. growth factors), proteins (e.g. enzymes, antibodies), oligonucleotides and nucleic acids (e.g. RNA, DNA, PNA, aptamers, spiegelmers), hormones and other natural substances or synthetic substances mimicking such, since many types of pharmacologically active biomolecules at least partially are broken down either in the digestive tract or in the blood system and are delivered suboptimally to the target site.

Therefore, an ongoing need exists for improved drug-delivery methods in the life sciences, including but not limited to human and veterinary medicine. One important goal for any new drug-delivery method is to deliver the desired therapeutic agent(s) to a specific place in the body over a specific and controllable period of time, i.e. controlling the delivery of one or more substances to specific organs and tissues in the body in both a spatial and temporal manner. Methods for accomplishing this spatially and temporally controlled delivery are known as controlled-release drug-delivery methods. Delivering APIs to specific organs and tissues in the body offers several potential advantages, including increased patient compliance, extending activity, lowering the required dose, minimizing side effects, and permitting the use of more potent therapeutics. In some cases, controlled-release drug-delivery methods can even allow the administration of therapeutic agents which would otherwise be too toxic or ineffective for use.

There are five broad types of solid dosage forms for controlled-delivery oral administration: reservoir and matrix diffusive dissolution, osmotic, ion-exchange resins, and pro-drugs. For parenterals, most of the above solid dosage forms are available as well as injections (intravenous, intramuscular, etc.), transdermal systems, and implants. Numerous products have been developed for both oral and parenteral administration, including depots, pumps, micro- and nano-particles.

The incorporation of APIs into polymer matrices acting as a core reservoir is one approach for controlling their delivery. Contemporary approaches for formulating such drug-delivery systems are dependent on technological capabilities as well as the specific requirements of the application. For sustained delivery systems there a two main structural approaches: the release controlled by diffusion through a barrier such as shell, coat, or membrane, and the release controlled by the intrinsic local binding strength of the API(s) to the core or to other ingredients in the core reservoir.

Another strategy for controlled delivery of therapeutic agents, especially for delivering biotherapeutics, involves their incorporation into polymeric micro- and nano-particles either by covalent or cleavable linkage or by trapping or adsorption inside porous network structures. Various particle architectures can be obtained, for instance core/shell structures. Typically one or more APIs are contained either in the core, in the shell, or in both components. Their concentration can be different throughout the respective component in order to modify the release pattern. Although polymeric nanospheres can be effective in the controlled delivery of APIs, they also suffer from several disadvantages. For example, their small size can allow them to diffuse in and out of the target tissue or being successfully attacked by macrophages. The use of intravenous nano-particles may also be limited due to rapid clearance by the reticuloendothelial system. Notwithstanding this, polymeric micro-spheres remain an important delivery vehicle.

In view of the above, there is a need for improving drug-delivery methods and compositions.

SUMMARY OF THE INVENTION

According to an embodiment, a method for manufacturing a drug-delivery composition is provided. The method includes providing at least a pharmaceutically active composition, including a hydrophobic matrix, and a liquid; and mixing the hydrophobic matrix and the pharmaceutically active composition to form a paste-like or semi-solid drug-delivery composition.

According to an embodiment, a drug-delivery composition is provided, which comprises a paste-like or semi-solid mixture including at least a hydrophobic matrix and a pharmaceutically active compound.

According to an embodiment, a method for delivery a drug-delivery composition is provided. The method includes providing a drug-delivery composition including a paste-like or semi-solid mixture comprising at least a hydrophobic matrix and a pharmaceutically active compound; and applying the drug-delivery composition into a human or animal body.

Those skilled in the art will recognize additional features and advantages upon reading the following detailed description, and upon viewing the accompanying drawings.

BRIEF DESCRIPTION OF THE DRAWINGS

The accompanying drawings are included to further an understanding of the embodiments that are incorporated in and constitute a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other.

DETAILED DESCRIPTION OF THE INVENTION

Figure 1:
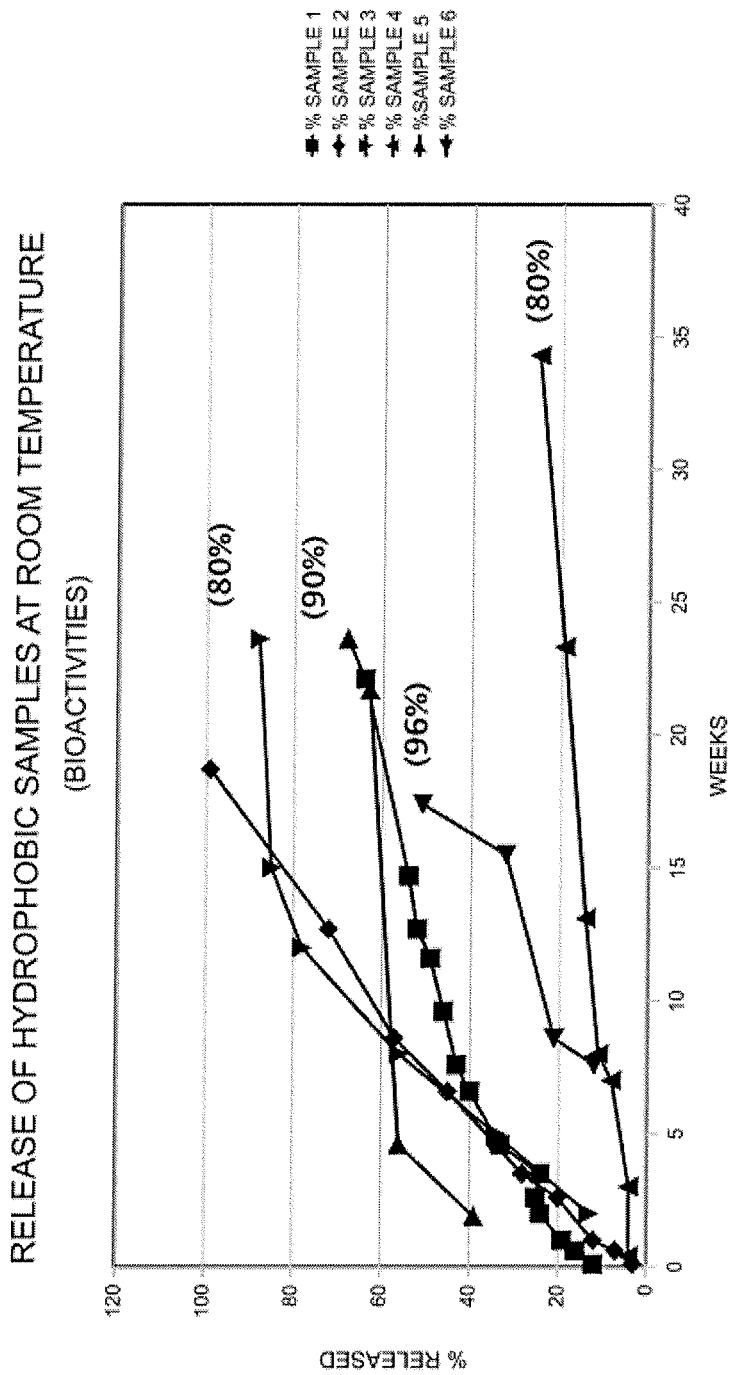
FIG. 1 illustrates release of antibodies from hydrophobic matrices at room temperature.

The following language and descriptions of certain preferred embodiments of the present invention are provided in order to further an understanding of the principles of the present invention. However, it will be understood that no limitations of the present invention are intended, and that further alterations, modifications, and applications of the principles of the present invention are also included.

For the purpose of this specification, the term "mixing" intends to describe a mechanical process or a mechanical treatment of the components. For example, mixing can be in the sense of carrying out repeated cycles of pressing and folding or comparable processing steps which lead to an intense compression and mixing of the provided hydrophobic matrices. The pharmaceutically active components are referred to hereinafter as active pharmaceutical ingredients (APIs).

According to an embodiment a drug-delivery composition is manufactured by providing at least a pharmaceutically active composition or API; providing a hydrophobic matrix; and mixing the hydrophobic matrix and the pharmaceutically active composition to form a paste-like or semi-solid drug delivery composition. An advantage of such a manufacturing method consists in achieving a sustained release formulation for pharmaceutically active ingredients with improved release characteristics. In particular, the method allows preparing drug-delivery compositions for sustained release of ingredients characterized by a specific biological activity which otherwise might decrease or even terminate.

According to an embodiment a drug-delivery composition is manufactured, wherein providing the hydrophobic matrix comprises mixing at least a hydrophobic solid component and a hydrophobic liquid component. Advantageously by mixing a given liquid hydrophobic component with a given solid hydrophobic component, allows preparing a wide range of consistencies i.e. rheological properties like viscosities of the paste-like or semi-solid composition depending on their quantitative relation. On the other hand, by carefully selecting a solid hydrophobic component and a liquid hydrophobic component, similar consistencies i.e. rheological properties, like viscosities of the paste-like or semi-solid composition can be achieved. Furthermore, depending on the type and quantity of the selected APIs, different hydrophobic components can be combined in order to form a paste-like or semi-solid composition with the desired properties.

According to an embodiment a drug delivery composition is manufactured, wherein the pharmaceutically active composition is provided as dry pharmaceutically active powder. Therein, the hydrophobic matrix is homogeneously mixed with the dry pharmaceutically active composition powder to form a paste-like or semi-solid drug-delivery composition. That allows arriving at a drug-delivery composition with the pharmaceutically active composition being homogeneously distributed within the hydrophobic matrix. Such drug-delivery compositions allow delivering the API over prolonged time periods.

According to an embodiment a drug delivery composition is manufactured, wherein the pharmaceutically active composition powder comprises particles in a size range from about 100 nm to about 50 μm. Such particle sizes are provided applying, e.g. lyophilized proteins.

According to an embodiment a drug delivery composition is manufactured, wherein the pharmaceutically active composition is provided in a solved state. It is homogeneously mixed with the hydrophobic matrix to form a paste-like or semi-solid drug-delivery composition. Advantageously, at least a solid hydrophobic substance and a liquid hydrophobic substance are mixed simultaneously with the dissolved API to form a paste-like or semi-solid drug-delivery composition. Optionally, the dissolved APIs can be added to the already premixed hydrophobic substances to form the paste-like or semi-solid drug-delivery composition.

According to an embodiment the drug-delivery composition is manufactured as described above, wherein the pharmaceutically active composition comprises at least the pharmaceutically active compound and at least one excipient selected from the group consisting of monosaccharides, disaccharides, oligosaccharides, polysaccharides like hyaluronic acid, pectin, gum arabic and other gums, albumin, chitosan, collagen, collagen-n-hydroxysuccinimide, fibrin, fibrinogen, gelatin, globulin, polyaminoacids, polyurethane comprising amino acids, prolamin, protein-based polymers, copolymers and derivatives thereof, and mixtures thereof. An advantage thereof consists in further modifying release characteristics of the drug-delivery paste-like or semi-solid composition.

According to an embodiment a drug delivery composition is manufactured, wherein the dissolved pharmaceutically active composition comprises at least a pharmaceutically active compound without any excipients.

According to an embodiment a drug-delivery paste-like or semi-solid composition is manufactured, wherein the forming of the paste-like or semi-solid drug-delivery composition includes repeated cycles of pressing and folding, e.g. pressing and folding in an algorithmic manner of the hydrophobic matrix itself and/or mixed with the pharmaceutically active composition.

According to an embodiment, no heating to transfer the hydrophobic solid component into a liquid state is used. In particular the solid hydrophobic matrix is kept throughout the mechanical treatment in a non-molten state.

According to an embodiment, active cooling is used in order to keep the hydrophobic matrix in a non-molten state throughout the pressing and folding cycles. This approach prevents self-organization processes to occur.

According to an embodiment the temperature of the mixture during pressing and folding cycles can be kept below a certain temperature value by cooling. Advantageously, that allows protecting susceptible biologically active substances such as proteins from denaturation, for instance by keeping the temperature of the mixture below 37° C., below 45° C., below 50° C., or especially below 60° C.

According to an embodiment the paste-like or semi-solid drug-delivery composition is manufactured by step-wise adding the dissolved APIs during repeated pressing and folding of the mixture of the hydrophobic substances forming the hydrophobic matrix. It is an advantage of that particular embodiment that the APIs can be distributed within the hydrophobic matrix homogeneously applying that process.

According to an embodiment of the manufacturing process pressures of not more than $10^6$ N·m$^{-2}$ are applied during the described pressing and folding cycles.

According to an embodiment a drug-delivery paste-like or semi-solid composition is manufactured using APIs in dissolved state, wherein the pharmaceutically active composition is dissolved in an aqueous solution before being mixed with the hydrophobic matrix.

According to an embodiment the paste-like or semi-solid drug-delivery composition is manufactured from APIs and hydrophobic components, wherein the pharmaceutically active composition is dissolved in an aqueous solution and is either simultaneously mixed with at least a hydrophobic solid component and a hydrophobic liquid component to form a paste-like or semi-solid drug-delivery composition; or the pharmaceutically active composition dissolved in an aqueous solution is added after the mixing of at least a hydrophobic solid component and at least a hydrophobic liquid component.

According to an embodiment the paste-like or semi-solid drug-delivery composition is manufactured from API(s) and hydrophobic components, wherein the hydrophobic matrix comprises a solid component and a liquid hydrophobic component. Therein the solid component is selected from waxes, fruit wax, carnauba wax, bees wax, waxy alcohols, plant waxes, soybean waxes, synthetic waxes, triglycerides, lipids, long-chain fatty acids and their salts like magnesium stearate, magnesium palmitate, esters of long-chain fatty acids, long-chain alcohols like cetyl palmitate, waxy alcohols, long-chain alcohols like cetylalcohol, oxethylated plant oils, oxethylated fatty alcohols.

According to an embodiment the pharmaceutically active composition for preparing the paste-like or semi-solid drug-delivery composition is selected from the group consisting of: immunoglobulins, fragments or fractions of immunoglobulins, synthetic substance mimicking immunoglobulins or fragments or fractions thereof, proteins, peptides having a molecular mass equal to or higher than 3.000 Dalton, ribonucleic acids (RNA), desoxyribonucleic acids (DNA), aptamers, spiegelmers, plasmids, peptide nucleic acids (PNA), steroids, and corticosteroids, and combinations thereof.

According to an embodiment, the pharmaceutically active compound can be one or more of immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists (e.g., anti TNF alpha, Interleukin-1, Interleukin-6 etc.), antiangiogenic compounds (e.g., anti-VEGF, anti-PDGF etc.), intracellular signaling inhibitors (e.g JAK1,3 and SYK inhibitors), peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a [beta]-adrenolytic, an androgen or antiandrogen, an antianemic, an anabolic, an anaesthetic, an analeptic, an antiallergic, an antiarrhythmic, an antiarteriosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a (para)-sympathicomimetic, a (para)-sympatholytic, a protein, a sedating agent, a spasmolytic, a vasoconstrictor, a vasodilatator, a vector, a virus, a virus-like particle, a virustatic, a wound-healing substance, and combinations thereof.

According to an embodiment a drug delivery composition is manufactured as described above, further comprising forming the drug-delivery composition into an applicable form. In particular, the resulting hydrophobic drug-delivery body can be transferred into the final dosage form, i.e. into bodies or micro-particles of desired shape, size and size distribution by means of colloid forming techniques and other technological procedures. Colloid forming techniques comprise e.g. milling, cold extruding, emulgating, dispersing, sonificating. The compositions formed by the methods described herein maintain the drug-releasing properties for a prolonged time such as weeks and months. The APIs remain protected in the paste-like or semi-solid mixture so that their specific biological activity can be maintained. If desired, additional barrier layers can be formed around the paste-like or semi-solid mixture.

According to an embodiment, a micro-porous membrane made from ethylene/vinyl acetate copolymer or other materials for ocular use can be formed around the paste-like or semi-solid mixture. Further options include use of biodegradable polymers for subcutaneous and intramuscular injection, bioerodible polysaccharides, hydrogels etc.

According to an embodiment a drug-delivery composition is provided, comprising a paste-like or semi-solid mixture comprising at least a hydrophobic matrix and a pharmaceutically active compound.

According to an embodiment a drug-delivery composition is provided, wherein the pharmaceutically active compound is dispersed in the hydrophobic matrix in particulate form.

According to an embodiment a drug-delivery composition is provided, wherein the pharmaceutically active compound is dispersed in the hydrophobic matrix in a dissolved state.

According to an embodiment a drug-delivery composition is provided, wherein the pharmaceutically active compound is dissolved in a solution comprising water and electrolytes.

According to an embodiment a drug-delivery composition is provided, wherein the pharmaceutically active compound is dissolved in a solution comprising water, electrolytes and at least one of monosaccharides, disaccharides, oligosaccharides, polysaccharides like hyaluronic acid, pectin, gum arabic and other gums, albumin, chitosan, collagen, collagen-n-hydroxysuccinimide, fibrin, fibrinogen, gelatin, globulin, polyaminoacids, polyurethane comprising amino acids, prolamin, protein-based polymers, copolymers and derivatives thereof, and mixtures thereof.

According to an embodiment a drug-delivery composition is provided, wherein the paste-like or semi-solid mixture has a modulus of elasticity at least of $10^{-4}$ N·mm$^{-2}$.

According to an embodiment a drug-delivery composition is provided, wherein the paste-like or semi-solid mixture has a viscosity of at least 100 mPa·s.

According to an embodiment a drug-delivery composition is provided, wherein the pharmaceutically active compound is selected from the group consisting of immunoglobulins, fragments or fractions of immunoglobulins, synthetic substances mimicking immunoglobulins or fragments or fractions thereof, therapeutic proteins, peptides having a molecular mass equal to or higher than 3 kDa, ribonucleic acids (RNA), desoxyribonucleic acids (DNA), plasmids, peptide nucleic acids (PNA), aptamers, spiegelmers, steroids, and corticosteroids, and combinations thereof.

According to an embodiment a drug-delivery composition is provided, wherein the pharmaceutically active compound is selected from the group consisting of: immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists (e.g., anti TNF alpha, Interleukin-1, Interleukin-6 etc.), antiangiogenic compounds (e.g., anti-VEGF, anti-PDGF etc.), intracellular signaling inhibitors (e.g JAK1,3 and SYK inhibitors), peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a [beta]-adrenolytic, an androgen or antiandrogen, an antianemic, an anabolic, an anaesthetic, an analeptic, an antiallergic, an antiarrhythmic, an antiarteriosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a (para)-sympathicomimetic, a (para)-sympatholytic, a protein, a sedating agent, a spasmolytic, a vasoconstrictor, a vasodilatator, a vector, a virus, a virus-like particle, a virustatic, a wound-healing substance, and combinations thereof.

According to an embodiment a drug-delivery composition is provided, wherein the hydrophobic matrix comprises at least a hydrophobic solid component and a hydrophobic liquid component, wherein the mass ratio of the hydrophobic solid component to the hydrophobic liquid component is below 2.8:1.

According to an embodiment a drug-delivery composition is provided, wherein the mass of the pharmaceutically active compound is up to 25% (w/w) of the total mass of the paste-like or semi-solid mixture.

According to an embodiment a drug-delivery composition is provided, wherein the mass of the pharmaceutically active compound is at least 0.1% (w/w) of the total mass of the paste-like or semi-solid mixture.

According to an embodiment a method for delivery a drug-delivery composition is suggested, comprising: providing a drug-delivery composition comprising a paste-like or semi-solid mixture comprising at least a hydrophobic matrix and a pharmaceutically active compound; and applying the drug-delivery composition into a human or animal body.

According to an embodiment a method for delivery a drug-delivery composition is suggested, wherein applying the mixture into the human or animal body comprises at least one of: implanting or injecting the mixture into a human or animal body; intraocular injecting the mixture into a human, or animal body; subcutaneous injecting the mixture into a human, or animal body; intramuscular injecting the mixture into a human, or animal body; and intraperitoneal injecting the mixture into a human, or animal body, intravenous injecting the mixture into a human, or animal body; inhalative or intranasal administration of the mixture into the human or animal body.

According to typical embodiments the described treatment of the hydrophobic matrices comprises intimate mixing a solid hydrophobic material and a liquid hydrophobic material with APIs to achieve an API-containing semi-solid material possessing superior controlled-delivery properties. According to an embodiment the API(s) are added to already treated hydrophobic matrices or at a late stage of their treatment, i.e their intimate mixing.

Surprisingly, the mechanical treatment comprising repeated pressing and folding cycles is slowing down the release kinetics and making the release of the API more sustained.

The suggested method of algorithmic processes of pressing and folding is especially suitable for formulating biologically active compounds. Biopolymers like proteins, peptides, poly- and oligonucleotides are particularly sensitive to changes in their environment and may lose their specific activity more readily than small-molecule APIs. Synthetic APIs and excipients mimicking biomacromolecules may carry both anionic and cationic groups in the relevant medium or may possess different functional groups in variable density on a molecular backbone.

The suggested approach combines the benefit of initial thorough mixing of the hydrophobic matrix with the controlled-release of microparticles but does not suffer from the disadvantages of any of these formulations when applied alone.

The matrix formed by the mechanical treatment of solid and liquid components is typically a hydrophobic matrix but can also include a small amount of hydrophilic excipients/ingredients.

The suggested method is different from other approaches in that the paste-like or semi-solid composition is formed by mechanical treatment, i.e. repeated pressing and folding cycles. Particularly, according to an embodiment, the paste-like or semi-solid composition is formed by kneading which is an example of an algorithmic pressing-folding cycle.

According to an embodiment, the pharmaceutically active substance or API is provided as dry pharmaceutically active compound powder. The solid and liquid hydrophobic components are homogeneously mixed with each other with or without the presence of the dry pharmaceutically active compound to prepare a sustained delivery body.

The mechanical procedures can include repeatedly pressing and folding the mixture of the hydrophobic solid and liquid materials. The mechanical procedures may start with pressing to bring the mass into a more flat shape and then folding the mass, for example by a blade or other suitable means. The folded mass is then pressed again. By repeating these processes a better distribution of the pharmaceutically active compound (API) throughout the matrix can be achieved.

The API(s) can be added to the treated system during all phases of the preparation process, and, according to an embodiment, at a late stage after forming an established excipient matrix system. The late addition of the APIs to the already homogenized mixture of hydrophobic constituents minimizes the influence of mechanical mixing on the APIs.

According to an embodiment, the mechanical processing of the mass can also include other processes such as rolling, extrusion from or through a nip between rolls.

The force acting on the mass may be limited to avoid excessive mechanical impact, which might affect the API. According to an embodiment, a pressure of not more than $10^6$ $N \cdot m^{-2}$ is applied to the mass. According to further embodiments, a pressure of not more than $5 \times 10^5 N \cdot m^{-2}$ is applied to the mass.

According to an embodiment, the mechanical treatment of the hydrophobic matrix components yields a homogeneous distribution of the API within the matrix.

The APIs may be provided as dry component or the APIs may be dissolved in an aqueous solution.

According to an embodiment, the APIs can be provided in particulate form such as micro- or nano-particles. Suitable particle sizes range from about 100 nm to about 50 μm, particularly from about 500 nm to about 30 μm, and more particularly from about 1 μm to about 10 μm.

In the approach described herein, the controlled mixing of the components into a homogeneous mass transforms the preparation into a paste- or dough-like consistency, which is appropriate for the production of slow release compositions. The processes according to one embodiment include mixing of all solid hydrophobic ingredients in a first step followed by adding the liquid hydrophobic matrix component to generate the paste-like or semi-solid consistency during mechanical treatment. The APIs is added, for instance as a dry powder into the paste like mass and the mechanical treatment is continued to gain homogeneity of the paste like mass.

According to an embodiment, APIs can be small molecules, peptides, proteins, therapeutic proteins, antibodies, antigens, enzymes, receptor ligands, nucleotides or nucleotide analogs, oligonucleotides and oligonucleotide analogs (aptamers and spiegelmers), genes or gene-like species, viruses, virus-like particles, sugars or polysaccharides or their analogs, or any other physical composition such as living organelles, cells, or tissue constituents.

According to an embodiment excipients can include almost any member of these same classes of species. They often act as buffer, filler, binder, osmotic agent, lubricant, or fulfill similar functions. Polyampholytes are multiply-charged polymers, which bear both anionic and cationic groups in the relevant medium, e.g. in an aqueous solution. The various classes and types of APIs, excipients, polymers, and polyampholytes are familiar to those skilled in the art of drug delivery.

According to an embodiment, an example for an excipient can be a sugar selected from monosaccharides, disaccharides, oligosaccharides, polysaccharides. The excipients can further comprise albumin, chitosan, collagen, collagen-n-hydroxysuccinimide, fibrin, fibrinogen, gelatin, globulin, polyaminoacids, polyurethane comprising amino acids, prolamin, protein-based polymers, copolymers and derivatives thereof, and mixtures thereof.

According to an embodiment, the pharmaceutically active compound can be one or more of immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists (e.g., anti TNF alpha, Interleukin-1, Interleukin-6 etc.), antiangiogenic compounds (e.g., anti-VEGF, anti-PDGF etc.), intracellular signaling inhibitors (e.g JAK1,3 and SYK inhibitors), peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a [beta]-adrenolytic, an androgen or antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a (para)-sympathicomimetic, a (para)-sympatholytic, a protein, a sedating agent, a spasmolytic, a vasoconstrictor, a vasodilatator, a vector, a virus, a virus-like particle, a virustatic, a wound-healing substance, and combinations thereof.

According to an embodiment, the drug-delivery composition can be brought into an implantable form to form an implantable drug-delivery formulation with controlled-release kinetics. According to the novel proposed approach the hydrophobic matrix itself can be comprised of natural waxes, fats and oils as well as synthetic substances or chemically modified natural waxes, fats and oils. The implantable drug-delivery formulation can be activated.

The present invention encompasses not only the use of pure hydrophobic matrix materials but can comprise also minor amounts of aqueous solutions. The method and composition described herein can use any substance which can exert a therapeutic effect, including small molecules, synthetic or biological macromolecules such as peptides, proteins, nucleic acids, oligonucleotides, carbohydrates, and others familiar to one skilled in the art.

The hydrophobic materials of the present invention can optionally be labeled with any of a wide variety of agents, which are known to those skilled in the art. As examples, dyes, fluorophores, chemiluminescent agents, isotopes, metal atoms or clusters, radionuclides, enzymes, antibodies, or tight-binding partners such as biotin and avidin can all be used to label the hydrophobic drug-delivery composition for detection, localization, imaging, or any other analytical or medical purpose. The hydrophobic delivery composition, particularly a liquid component of the matrix, can also optionally be conjugated with a wide variety of molecules in order to modify its function, modify its stability, or further modify the rate of release of the APIs. As examples, the drug-delivery composition can be coated with a covalently- or non-covalently-attached layer of a species such as small molecules, hormones, peptides, proteins, phospholipids, polysaccharides, mucins, or biocompatible polymers such polyethylene glycol (PEG), dextran, or any of a number of comparable materials. The wide range of materials, which can be used in this fashion, and the methods for accomplishing these processes, are well known to those skilled in the art.

The various starting components such as the hydrophobic matrix and the APIs can be further manipulated and processed using a wide variety of methods, processes, and equipment familiar to one skilled in the art. For example, the hydrophobic matrix components can be thoroughly mixed using any of a number of known methods and equipment, such as trituration with a mortar and pestle or blending in a Patterson-Kelley twin-shell blender, before adding the API. Furthermore, a wide variety of shapes, sizes, morphologies, and surface compositions of the drug-delivery composition can be formed. For example, micro-particles or cylindrical bodies with different aspect ratios can be prepared by means of mechanical milling, molding, and extruding or similar processes of the paste-like or semi-solid or even semi-solid material. The resulting particles can be further treated to prepare them for specific applications such as e.g. drug delivery systems. As another example, transforming the mixture, paste or mass into micro-particles or bodies by means of cold extrusion, cooled pressure homogenization, molding, and/or other such well-established procedures can yield a wide range of final products. As another example, the polymeric drug-delivery composition can be squeezed through a sieving disk (i.e. a die) containing predefined pores or channels with uniform pore geometry and diameter by an extrusion process.

According to an embodiment, the paste-like or semi-solid mixture drug-delivery composition has a modulus of elasticity of at least $10^{-4}$ N·mm$^{-2}$. According to an embodiment, the paste-like or semi-solid mixture drug-delivery composition has a modulus of elasticity of at least $10^{-3}$ N·mm$^{-2}$, and particularly $10^{-2}$ N·mm$^{-2}$, and more particularly $10^{-1}$ N·mm$^{-2}$.

According to an embodiment, the paste-like or semi-solid mixtures has a viscosity of not more than 500 Pa·s, and particularly of not more than 250 Pa·s. According to an embodiment, the paste-like or semi-solid mixtures has a viscosity of not less than few mPa·s, for example 100 mPa·s, and particularly of not less than 1 Pa·s.

According to an embodiment, the pharmaceutical active compound is provided as powder having particles in a range from about 100 nm to about 50 μm, particularly from about 500 nm to about 30 μm, and more particularly from about 1 μm to about 10 μm Specific examples are described below. The "UV 280 nm method" mentioned therein comprises the detection of proteins by their absorption at 280 nm in physiologically isotonic salt solution (PBS) against a blank using an UV/VIS spectrophotometer and quartz cuvettes and using calibrations for different APIs and different concentrations.

Example 1

72 mg of an antibody 2 (of gamma globulin type) solution (25 mg/ml) was added to 170 mg of cetyl alcohol and 50 mg of castor oil. This mixture was mechanically treated and mixed using an agate mortar and pestle for 7 minutes. Finally, a spherical particle was formed by hand and added to 3.3 g of an isotonic sodium chloride solution containing 0.01% of sodium azide. The release of antibody 1 was determined spectroscopically by the UV 280 nm method under no-sink conditions (see FIG. 1, sample 1).

Example 2

72 mg of a lyophilized antibody 3 (of gamma globulin type) was added to 90 mg of cetyl alcohol and 50 mg of castor oil. This mixture was mechanically treated and mixed using an agate mortar and pestle for 5 minutes. Finally, a spherical particle was formed by hand and added to 10 g of an isotonic sodium chloride solution containing 0.01% of sodium azide. The release of antibody 3 was determined spectroscopically by the UV 280 nm method under no-sink conditions (see FIG. 1, sample 2).

Example 3

100 mg of a solution of antibody 1 (of gamma globulin type) (50 mg/ml) was added to 95 mg of cetyl alcohol and 75 mg of castor oil. This mixture was mechanically treated and mixed using an agate mortar and pestle for 7 minutes. Finally, a spherical particle was formed by hand and added to 6.4 g of an isotonic sodium chloride solution containing 0.01% of sodium azide. The release of antibody 2 was determined spectroscopically by the UV 280 nm method under no-sink conditions. The biological activity of the last measured concentration value was measured by ELISA as given in brackets (see FIG. 1, sample 3).

Example 4

76 mg of an antibody solution antibody 2 (of gamma globulin type) (25 mg/ml) was added to 170 mg of cetyl alcohol and 45 mg of soybean oil. This mixture was mechanically treated using an agate mortar and pestle for 6 minutes. Finally, a spherical particle was formed by hand and added to 3.3 g of a phosphate buffered solution containing 0.01% of sodium azide. The release of antibody 1 was determined spectroscopically by the UV 280 nm method under sink conditions. The biological activity of the last measured concentration value was measured by ELISA as given in brackets (see FIG. 1, sample 4).

Example 5

101 mg of an antibody solution antibody 1 (of gamma globulin type) (25 mg/ml) was added to 101 mg of cetyl alcohol and 80 mg of soybean oil. This mixture was mechanically treated using an agate mortar and pestle for 7 minutes. Finally, a spherical particle was formed by hand and added to 5.7 g of a phosphate buffered solution containing 0.01% of sodium azide. The release of antibody 2 was determined spectroscopically by the UV 280 nm method under sink conditions. The biological activity of the last measured concentration value was measured by ELISA as given in brackets (see FIG. 1, sample 5).

Example 6

116 mg of an antibody solution antibody 2 (of gamma globulin type) (25 mg/ml) was added to 170 mg of magnesium stearate and 78 mg of soybean oil. This mixture was mechanically treated using an agate mortar and pestle for 7 minutes. Finally, a spherical particle was formed by hand and added to 5.7 g of a phosphate buffered solution containing 0.01% of sodium azide. The release of antibody 1 was determined spectroscopically by the UV 280 nm method under sink conditions. The biological activity of the last measured concentration value was measured by ELISA as given in brackets (see FIG. 1, sample 6).

Example 7

Figure 2:
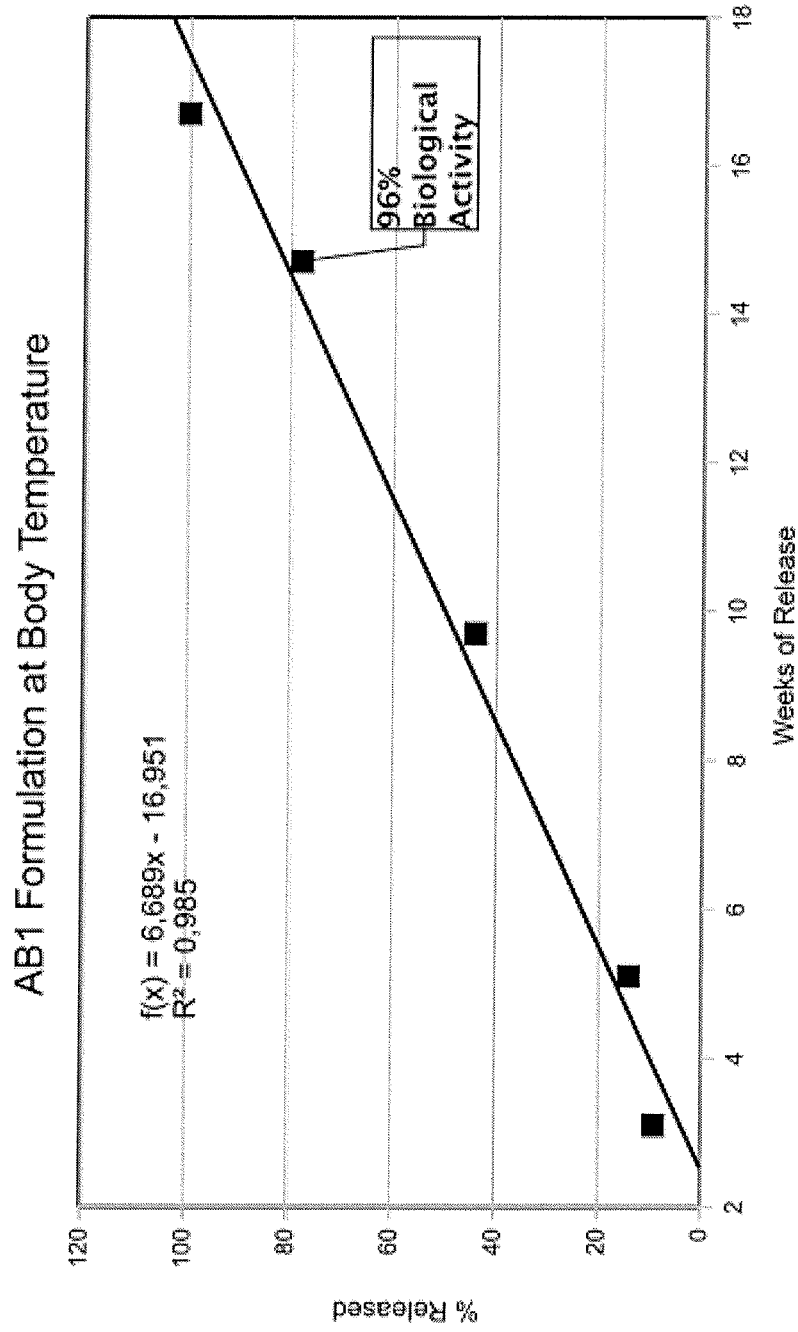
FIG. 2 illustrates release of antibody 2 from a hydrophobic matrix at body temperature.

98 mg of an antibody solution antibody 1 (of gamma globulin type) (50 mg/ml) was added to 97 mg of magnesium stearate and 79 mg of soybean oil. This mixture was mechanically treated using an agate mortar and pestle for 7 minutes. Finally, a spherical particle was formed by hand and added to 4.2 g of a phosphate buffered solution containing 0.01% of sodium azide. The sample was stored at 37° C. for the experimental period. The release of antibody was determined spectroscopically by the UV 280 nm method under sink conditions. The biological activity of the last measured concentration value was measured by ELISA as indicated in brackets (see FIG. 2).

Figure 3:
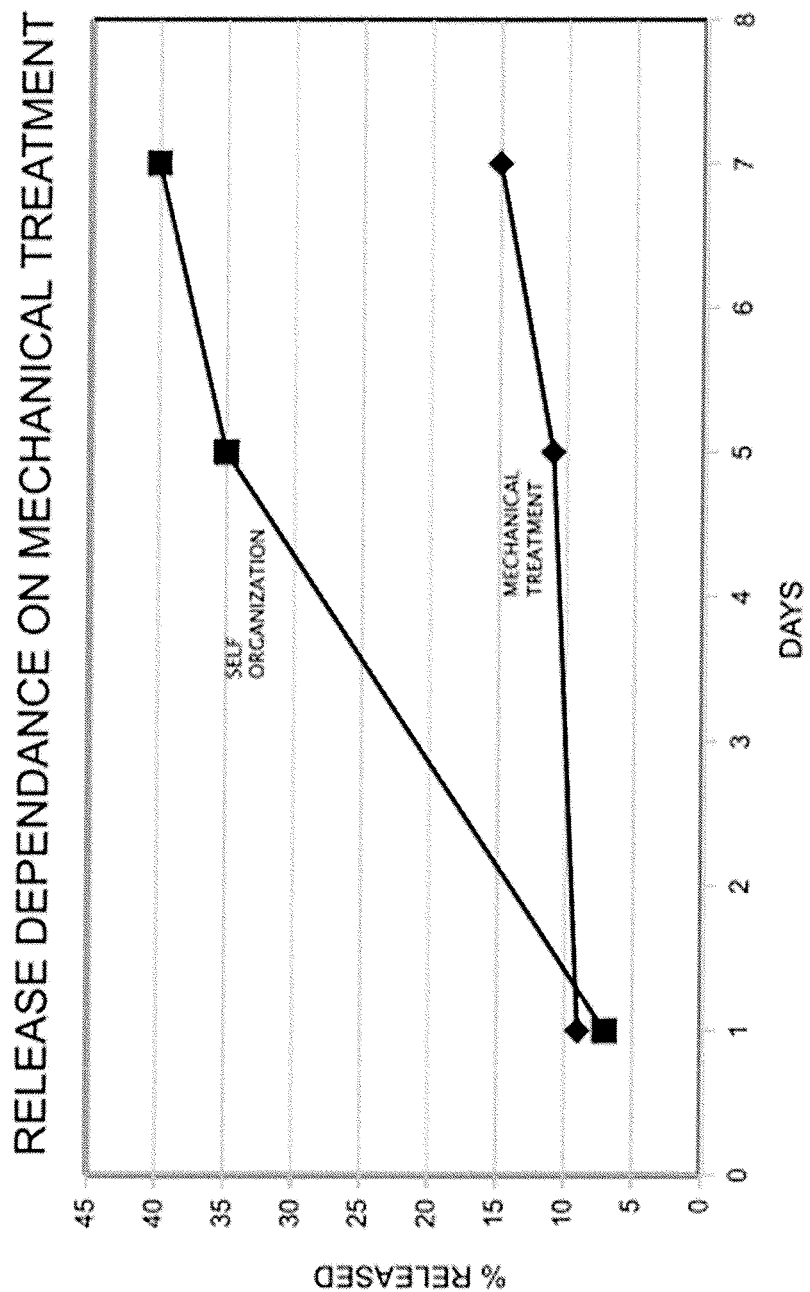
FIG. 3 shows a comparison between the mechanically treated antibody 3 releasing hydrophobic matrix and self-organized antibody 3—releasing hydrophobic matrix.

The difference between mechanically treated drug delivery matrices and the self-organized ones have been studied in example 8 below and is illustrated in FIG. 3.

Example 8

Self Organization 13 mg of a lyophilized antibody 3 (of gamma globulin type) was added to 93 mg of cetyl palmitate and 48 mg of castor oil. This mixture was homogenized by heating under stirring using a water bath and a magnetic stirrer to form a molten mass (45° C.). After cooling down the obtained solid mass was added to 3.0 g of a phosphate buffered solution containing 0.1% of sodium azide. The release of antibody 3 was determined spectroscopically by the UV 280 nm method under sink conditions (see FIG. 3, sample 8).

Example 9

Mechanical Treatment 11 mg of a lyophilized antibody 3 (of gamma globulin type) was added to 83 mg of cetyl palmitate and 38 mg of castor oil. This mixture was mechanically treated and mixed using an agate mortar and pestle for 7 minutes. Finally, a spherical particle was formed by kneading for 1 minute and added to 3.0 g of a phosphate buffered solution containing 0.1% of sodium azide. The release of antibody 3 was determined spectroscopically by the UV 280 nm method under sink conditions (see FIG. 3, sample 9).

The invention claimed is:

1. A method for manufacturing a sustained release drug-delivery composition, comprising:
providing at least a pharmaceutically active composition dissolved in an aqueous solution;
providing a hydrophobic matrix comprising at least a hydrophobic solid component and a hydrophobic liquid component, wherein the hydrophobic matrix is formed by mechanical treatment of the hydrophobic solid component and the hydrophobic liquid component, said mechanical treatment comprising repeated pressing and folding, wherein the hydrophobic matrix is kept in a non-molten state throughout the mechanical treatment;
mixing the hydrophobic matrix and the pharmaceutically active composition dissolved in an aqueous solution to form a paste-like or semi-solid drug-delivery composition, said mixing comprising repeated pressing and folding of the hydrophobic matrix and the pharmaceutically active composition to form the paste-like or semi-solid drug-delivery composition, wherein the pressing applies a pressure of not more than $10^8$ N·m$^{-2}$, wherein the hydrophobic matrix is kept in a non-molten state throughout the mixing; and
wherein the pharmaceutically active composition dissolved in an aqueous solution comprises a pharmaceutically active compound selected from the group consisting of humanized monoclonal antibodies and human monoclonal antibodies.

2. The method according to claim 1, wherein the pharmaceutically active composition comprises at least one excipient selected from the group consisting of monosaccharides, disaccharides, oligosaccharides, polysaccharides, hyaluronic acid, pectin, gum arabic and other gums, albumin, chitosan, collagen, collagen-n-hydroxysuccinimide, fibrin, fibrinogen, gelatin, globulin, polyaminoacids, polyurethane comprising amino acids, prolamin, protein-based polymers, copolymers and derivatives thereof, and mixtures thereof.

3. The method according to claim 1, wherein the pharmaceutically active composition comprises at least a pharmaceutically active compound without any excipients.

4. The method according to claim 1, wherein the forming of the paste-like or semi-solid drug-delivery composition includes repeated cycles of pressing and folding, in an algorithmic manner, of the mixture of the hydrophobic matrix and the pharmaceutically active composition.

5. The method according to claim 1, further comprising:
forming the drug-delivery composition into an applicable form.

6. The method according to claim 1, wherein active cooling is used in order to keep the hydrophobic matrix in a non-molten state throughout the repeated pressing and folding.

7. The method according to claim 1, wherein the temperature of the pharmaceutically active composition is kept below 60° C. during repeated pressing and folding.

8. The method according to claim 1, wherein the temperature of the pharmaceutically active composition is kept below 50° C. during repeated pressing and folding.

9. The method according to claim 1, wherein the temperature of the pharmaceutically active composition is kept below 45° C. during repeated pressing and folding.

10. The method according to claim 1, wherein the temperature of the pharmaceutically active composition is kept below 37° C. during repeated pressing and folding.

11. The method according to claim 1, wherein the pharmaceutically active composition dissolved in an aqueous solution is added step-wise during mixing.

12. A method for manufacturing a sustained release drug-delivery composition, comprising:
providing at least a pharmaceutically active composition dissolved in aqueous solution;
providing at least a hydrophobic solid component;
providing at least a hydrophobic liquid component;
simultaneous mixing of at least the pharmaceutically active composition dissolved in an aqueous solution, the hydrophobic solid component, and the hydrophobic liquid component to form a paste-like or semi-solid drug-delivery composition, said mixing comprising repeated pressing and folding, wherein the pressing applies a pressure of not more than $10^5$ N·m$^{-2}$, wherein the hydrophobic solid component is kept in a non-molten state throughout the mixing; and
wherein the pharmaceutically active composition dissolved in an aqueous solution comprises a pharmaceutically active compound selected from the group consisting of humanized monoclonal antibodies and human monoclonal antibodies.

13. The method according to claim 12, wherein active cooling is used in order to keep the hydrophobic solid component in a non-molten state throughout the mixing.

14. The method according to claim 12, wherein the temperature of the pharmaceutically active composition is kept below 60° C. during repeated pressing and folding.

15. The method according to claim 12, wherein the temperature of the pharmaceutically active composition is kept below 50° C. during repeated pressing and folding.

16. The method according to claim 12, wherein the temperature of the pharmaceutically active composition is kept below 45° C. during repeated pressing and folding.

17. The method according to claim 12, wherein the temperature of the pharmaceutically active composition is kept below 37° C. during repeated pressing and folding.

18. The method according to claim 12, wherein the mass ratio of the hydrophobic solid component to the hydrophobic liquid component is below 2.8:1.

* * * * *